United States Patent
Umemoto et al.

(10) Patent No.: US 11,018,608 B2
(45) Date of Patent: May 25, 2021

(54) SELF-PROPELLED ENDOSCOPE APPARATUS AND CONTROL APPARATUS FOR THE SAME

(71) Applicant: OLYMPUS CORPORATION, Tokyo (JP)

(72) Inventors: Yoshitaka Umemoto, Hachioji (JP); Takashi Suzuki, Hino (JP); Fumiyuki Onoda, Tama (JP); Takashi Yamashita, Hachioji (JP); Yasuaki Natori, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/735,823

(22) Filed: Jan. 7, 2020

(65) Prior Publication Data
US 2020/0144945 A1 May 7, 2020

Related U.S. Application Data

(63) Continuation of application No. PCT/JP2018/018097, filed on May 10, 2018.

(30) Foreign Application Priority Data

Jul. 7, 2017 (JP) .............................. JP2017-133495

(51) Int. Cl.
*H02P 6/30* (2016.01)
*A61B 1/00* (2006.01)
*H02P 6/12* (2006.01)

(52) U.S. Cl.
CPC ............ *H02P 6/30* (2016.02); *A61B 1/00006* (2013.01); *A61B 1/0016* (2013.01); *A61B 1/00156* (2013.01); *H02P 6/12* (2013.01)

(58) Field of Classification Search
USPC ....................................................... 318/560
See application file for complete search history.

(56) References Cited

U.S. PATENT DOCUMENTS 4,967,133 A * 10/1990 Hasegawa ................ H02H 7/08
318/759
5,595,565 A * 1/1997 Treat ................... A61B 1/00156
600/101

(Continued)

FOREIGN PATENT DOCUMENTS

| JP | 2009-055956 A | 3/2009 |
| JP | 2010-241308 A | 10/2010 |
| WO | WO 2016/104073 A1 | 6/2016 |

OTHER PUBLICATIONS

English translation of International Preliminary Report on Patentability dated Jan. 16, 2020, together with the Written Opinion received in related International Application No. PCT/JP2018/018097.

(Continued)

*Primary Examiner* — Bentsu Ro
(74) *Attorney, Agent, or Firm* — Scully, Scott, Murphy & Presser, P.C.

(57) ABSTRACT

A self-propelled endoscope apparatus includes a rotation body, a motor, a drive circuit, and a regeneration protection circuit. The rotation body is provided on an outer peripheral surface of an elongated insertion section. The rotation body is configured to be rotatable. The motor rotates the rotation body. The drive circuit drives the motor. The regeneration protection circuit performs protecting operation for protecting the drive circuit from regeneration voltage generated by regeneration of the motor.

14 Claims, 3 Drawing Sheets

(56) References Cited

U.S. PATENT DOCUMENTS

| | | | |
|---|---|---|---|
| 6,224,544 B1 * | 5/2001 | Takada | A61B 1/121 600/101 |
| 2004/0260150 A1 * | 12/2004 | Bernstein | A61B 1/0053 600/139 |
| 2007/0208299 A1 | 9/2007 | Breedveld | |
| 2009/0209812 A1 * | 8/2009 | Omoto | A61B 1/00158 600/110 |
| 2020/0138266 A1 * | 5/2020 | Suzuki | A61B 1/00133 |

OTHER PUBLICATIONS

International Search Report dated Jun. 19, 2018 issued in PCT/JP2018/018097.

* cited by examiner

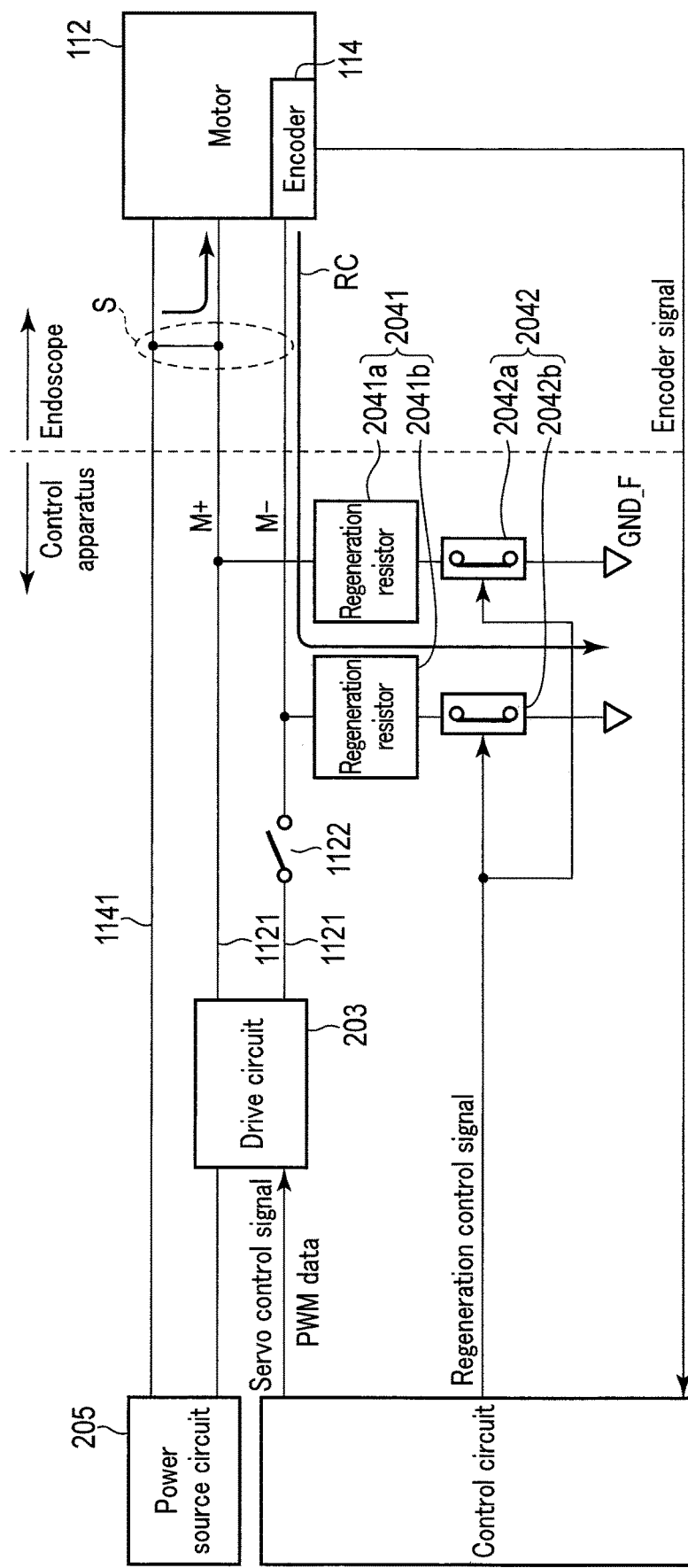
F I G. 2

SELF-PROPELLED ENDOSCOPE APPARATUS AND CONTROL APPARATUS FOR THE SAME

CROSS-REFERENCE TO RELATED APPLICATIONS

This application is a Continuation Application of PCT Application No. PCT/JP2018/018097, filed May 10, 2018 and based upon and claiming the benefit of priority from the prior Japanese Patent Application No. 2017-133495, filed Jul. 7, 2017, the entire contents of both of which are incorporated herein by reference.

FIELD

The embodiment relates to a self-propelled endoscope apparatus and a control apparatus for the same.

BACKGROUND

Self-propelled endoscope apparatuses proposed in Jpn. Pat. Appln. KOKAI Publication No. 2009-055956, and the like are known as endoscope apparatuses to be inserted into a lumen. In the self-propelled endoscope apparatus, for example, an insertion section is moved forward and backward by a propulsive force generated by rotating a rotation body provided around the insertion section by a motor. Such an endoscope apparatus assists an insertion or removal operation of the insertion section by the user.

SUMMARY

According to an aspect, a self-propelled endoscope apparatus comprises a rotation body, a motor, a drive circuit, and a regeneration protection circuit. The rotation body is provided on an outer peripheral surface of an elongated insertion section. The rotation body is configured to be rotatable. The motor rotates the rotation body. The drive circuit drives the motor. The regeneration protection circuit performs protecting operation for protecting the drive circuit from regeneration voltage generated by regeneration of the motor.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 2 is a diagram for explaining a configuration of a regeneration protection circuit.

DETAILED DESCRIPTION

Figure 1:
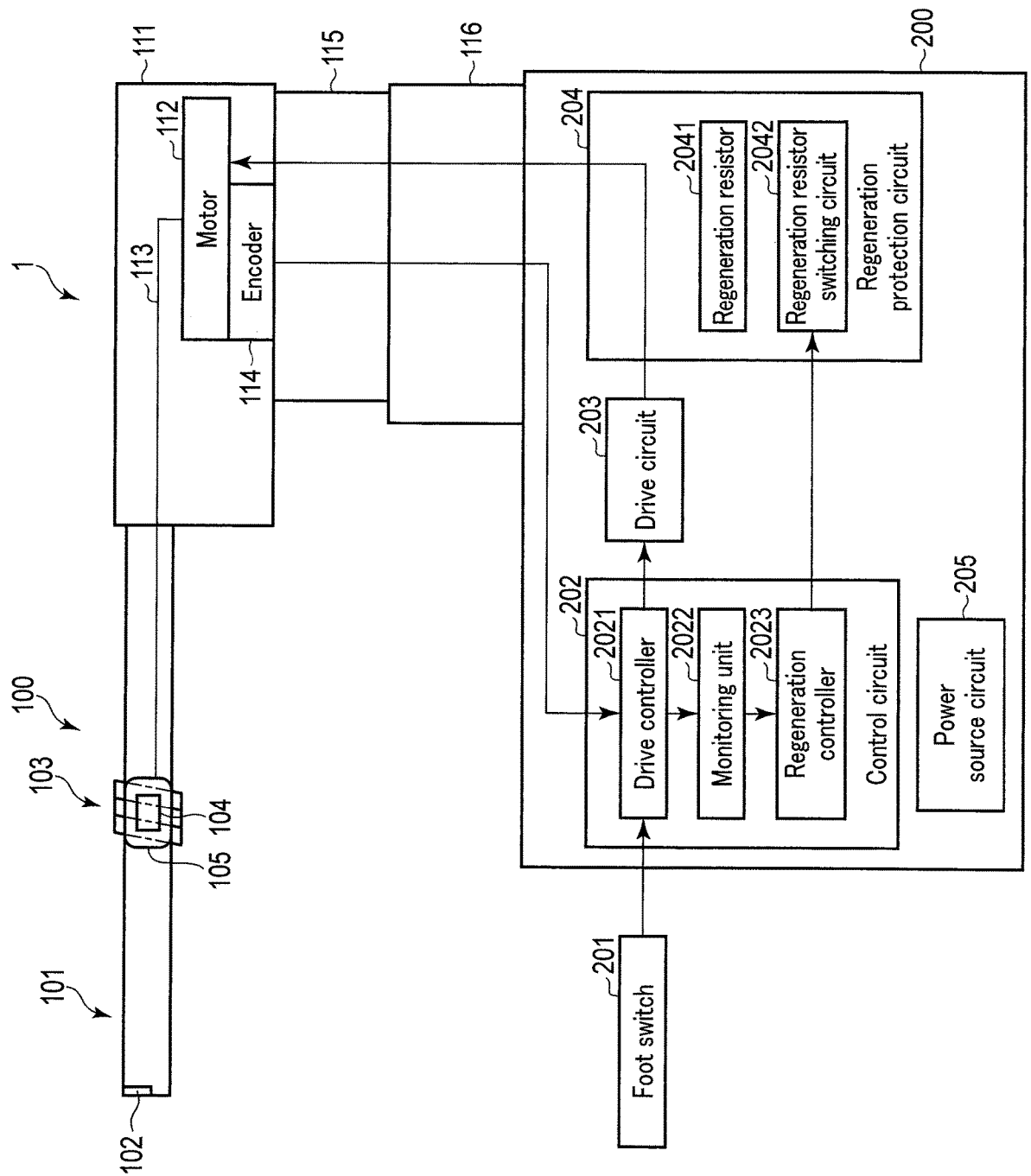
FIG. 1 is a diagram illustrating a configuration example of an endoscope apparatus according to an embodiment.

An embodiment will be described below with reference to the drawings. FIG. 1 is a diagram illustrating a configuration example of an endoscope apparatus according to an embodiment. An endoscope apparatus 1 comprises an endoscope 100 and a control apparatus 200. The endoscope 100 is configured to be connected to the control apparatus 200 via a connector 116 provided on the endoscope 100.

The endoscope 100 is a self-propelled endoscope apparatus including an insertion section 101 and an operation unit 111.

The insertion section 101 is a distal end portion of the endoscope 100. The insertion section 101 has an elongated shape and is configured to be flexible. Furthermore, an imager 102 is provided at the distal end of the insertion section 101. The imager 102 images a subject existing on the distal end side of the insertion section 101 and acquires image data about the subject. Furthermore, the insertion section 101 is provided with a moving mechanism 103. The moving mechanism 103 comprises a rotation body 104 and a spiral tube 105. The rotation body 104 is provided on an outer peripheral surface of the insertion section 101 so as to be rotatable around a longitudinal axis. The spiral tube 105 is provided so as to have a spiral fin around the rotation body 104. The spiral tube 105 may be configured to be removable from the rotation body 104. The spiral tube 105 may also be configured to be disposable.

The operation unit 111 is a part that is gripped by the user, and comprises various operation members for operating the endoscope 100. Furthermore, the operation unit 111 comprises a motor 112. The motor 112 generates a driving force for the moving mechanism 103. When the motor 112 rotates, the rotational motion is transmitted to the rotation body 104 via a transmission member 113 extending from the inside of the operation unit 111 to the insertion section 101. As the rotation body 104 rotates, the spiral tube 105 rotates. Due to the rotation of the spiral tube 105, a propulsive force is generated in the insertion section 101. This propulsive force causes the insertion section 101 to self-propel. The self-propulsion of the insertion section 101 assists in the tasks of insertion and removal of the insertion section 101 by the user. Furthermore, for example, a rotary encoder 114 is provided near the motor 112. The encoder 114 outputs an encoder signal corresponding to the rotating speed of the motor 112. The encoder signal includes an encoder phase A signal and an encoder phase B signal. The encoder phase A signal and the encoder phase B signal are different from each other in phase by 90 degrees.

A universal cable 115 is connected to the operation unit 111. The universal cable 115 is provided with various signal lines for transmitting and receiving signals between the endoscope 100 and the control apparatus 200. The universal cable 115 is connected to the connector 116. As described above, the endoscope 100 and the control apparatus 200 are connected via the connector 116.

The control apparatus 200 comprises a foot switch 201, a control circuit 202, a drive circuit 203, a regeneration protection circuit 204, and a power source circuit 205.

The foot switch 201 comprises a forward pedal and a backward pedal. When the forward pedal is stepped on by the user, the forward pedal generates an operating state signal for causing the motor 112 to rotate forward. The backward pedal generates an operating state signal for reversing the rotation of the motor 112 when stepped on by the user. The foot switch 201 may be configured to generate an operating state signal having a strength corresponding to the amount of depression.

The control circuit 202 is a control circuit comprising pieces of hardware including an FPGA and a CPU, and the like and controls the operation of sections of the control apparatus 200 such as the drive circuit 203 and the regeneration protection circuit 204. The control circuit 202 comprises a drive controller 2021, a monitoring unit 2022, and a regeneration controller 2023. The control circuit 202 may comprise a single FPGA or comprise a plurality of FPGAs and the like. Some of the functions of the control circuit 202 may be implemented in a form of software.

The drive controller 2021 controls the drive circuit 203 to drive the motor 112 at a rotating speed corresponding to a body load. For example, the drive controller 2021 receives the encoder signal output from the encoder 114. The drive controller 2021 then generates PWM data for controlling the magnitude of the voltage output from the drive circuit 203 so that the actual rotating speed of the motor 112 detected from the encoder signal matches the rotating speed corresponding to the amount of depression of the foot switch 201. The rotating speed corresponding to the amount of depression of the foot switch 201 is a rotating speed corresponding to the operating state signal. The drive controller 2021 then turns on a servo control signal for starting the drive of the motor 112 by the drive circuit 203 and inputs the servo control signal into the drive circuit 203 together with the PWM data. The drive controller 2021 inputs the servo control signal and the encoder signal into the monitoring unit 2022.

The monitoring unit 2022 monitors the operating state of the motor 112 and inputs the monitoring result into the regeneration controller 2023. Here, the operating state of the motor 112 includes the state of the servo control signal and the actual rotating speed of the motor 112. The state of the servo control signal includes the state of whether the motor is controlled by the drive controller 2021. When the servo control signal is on, the monitoring unit 2022 detects that the motor 112 is controlled, and when the servo control signal is off, the monitoring unit 2022 detects that the motor 112 is not controlled. Furthermore, the monitoring unit 2022 detects the rotating speed of the motor 112 based on the encoder signal.

The regeneration controller 2023 controls the regeneration protection circuit 204 based on the monitoring result from the monitoring unit 2022. When the control of the motor by the drive controller 2021 is stopped, the regeneration controller 2023 starts the protecting operation by the regeneration protection circuit 204, which will be described below in detail. The regeneration controller 2023 then ends the protecting operation by the regeneration protection circuit 204 after a lapse of a predetermined set time since the motor 112 is actually stopped by stopping the control of the motor by the drive controller 2021.

The drive circuit 203 generates a voltage to be supplied to the motor 112 according to the PWM data included in the servo control signal from the drive controller 2021 and applies the generated voltage to the motor 112.

The regeneration protection circuit 204 is provided in a path between the motor 112 and the drive circuit 203, and performs the protecting operation for protecting the sections of the control apparatus 200 from a regeneration voltage occurring by the regeneration in the motor 112. This regeneration protection circuit 204 comprises a regeneration resistor 2041 and a regeneration resistor switching circuit 2042. The regeneration resistor 2041 is a resistance that comprises one end being connected in parallel to a power source line connecting the motor 112 and the drive circuit 203 and comprises another end being grounded. The regeneration resistor switching circuit 2042 is a switch that is provided between the regeneration resistor 2041 and a ground (GND_F) and short-circuits or opens between the regeneration resistor 2041 and the ground (GND_F) according to a regeneration control signal from the regeneration controller 2023 of the control circuit 202. The regeneration protection circuit 204 will be described below in detail.

The power source circuit 205 comprises, for example, an AC power supply and converts the electric power of this AC power supply into electric power needed by the sections of the control apparatus 200. The power source circuit 205 then supplies the converted electric power to the sections of the control apparatus 200. Furthermore, the power source circuit 205 also supplies electric power to the motor 112, the encoder 114, and the like of the endoscope 100.

The regeneration protection circuit 204 will be described below more in detail. FIG. 2 is a diagram for explaining a configuration of a regeneration protection circuit. As described above, the regeneration protection circuit 204 is provided in the path between the motor 112 and the drive circuit 203. In the example illustrated in FIG. 2, the motor 112 and the drive circuit 203 are connected via motor power source lines 1121. The motor power source lines 1121 comprise a power source line (M+) connected to the positive (+) terminal of the motor 112 and a power source line (M−) connected to the negative (−) terminal of the motor 112. When the drive circuit 203 causes current to flow from the power source line M+ to the power source line M−, the motor 112 rotates forward. Conversely, when the drive circuit 203 flows current from the power source line M− to the power source line M+, the motor 112 rotates backward. Furthermore, the power source line M− is provided with a motor relay 1122. The motor relay 1122 brings the power source line M− into a connected state when the servo control signal is on, and the motor relay 1122 brings the power source line M− into a disconnected state when the servo control signal is off. When the power source line M− is in the disconnected state, the motor 112 is in a free state where the motor 112 is not supplied with the electric power from the drive circuit 203. When the motor 112 is in the free state, the motor 112 freely rotates by receiving, for example, an external force from the body.

In the example illustrated in FIG. 2, the regeneration resistor 2041 of the regeneration protection circuit 204 comprises a first regeneration resistor 2041a that is connected in parallel to the power source line M+ being a first power source line and a second regeneration resistor 2041b that is connected in parallel to the power source line M− being a second power source line. The first regeneration resistor 2041a is connected to the ground (GND_F) via a first regeneration resistor switching circuit 2042a that constitutes the regeneration resistor switching circuit 2042. The second regeneration resistor 2041b is connected to the ground (GND_F) via a second regeneration resistor switching circuit 2042b that constitutes the regeneration resistor switching circuit 2042. Note that the first regeneration resistor 2041a and the second regeneration resistor 2041b are desirably resistors having the same resistance value and the same structure.

The first regeneration resistor switching circuit 2042a and the second regeneration resistor switching circuit 2042b are each turned on or off according to the regeneration control signal from the control circuit 202. When the first regeneration resistor switching circuit 2042a is turned on, the first regeneration resistor 2041a is short-circuited to the ground. In contrast, when the first regeneration resistor switching circuit 2042a is turned off, the first regeneration resistor 2041a is opened. Similarly, when the second regeneration resistor switching circuit 2042b is turned on, the second regeneration resistor 2041b is short-circuited to the ground. In contrast, when the second regeneration resistor switching circuit 2042b is turned off, the second regeneration resistor 2041b is opened. Note that, in the example illustrated in FIG. 2, the first regeneration resistor 2041a and the second regeneration resistor 2041b are earthed or opened simultaneously. Of course, the first regeneration resistor 2041a and the second regeneration resistor 2041b may be configured to be separately earthed or opened.

Here, for decreasing the diameter of the universal cable 115 or for other purposes, an encoder power source line 1141 is disposed near the motor power source lines 1121, as illustrated in FIG. 2. The encoder power source line 1141 is a power source line connecting the encoder 114 and the power circuit 205 and transmits electric power for the encoder 114 generated in the power circuit 205 to the encoder 114.

Figure 3:
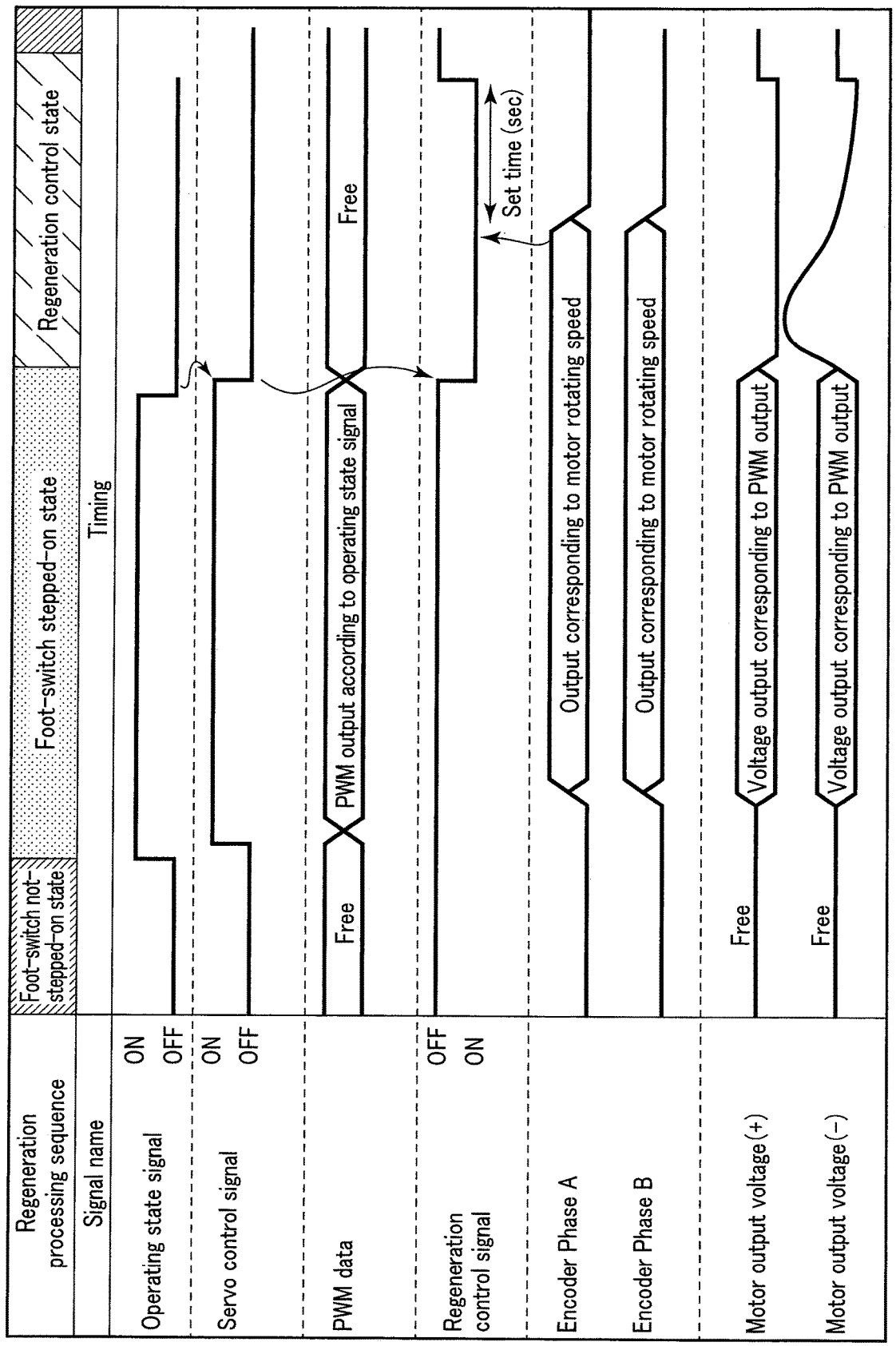
FIG. 3 is a timing chart relating to regeneration processing for an endoscope apparatus.

The operation of the endoscope apparatus 1 in the embodiment will be described below. FIG. 3 is a timing chart relating to regeneration processing for the endoscope apparatus 1. Here, "OPERATING STATE SIGNAL" illustrated in FIG. 3 indicates the on-state or the off-state of the foot switch 201. "SERVO CONTROL SIGNAL" indicates the on-state or the off-state of the servo control signal. "PWM DATA" indicates the state of the PWM data transmitted to the drive circuit 203. "REGENERATION CONTROL SIGNAL" indicates the on-state or the off-state of the regeneration control signal. "ENCODER PHASE A" indicates the state of the encoder phase A signal. "ENCODER PHASE B" indicates the state of the encoder phase B signal. "MOTOR OUTPUT VOLTAGE (+)" indicates the voltage of the power source line M+. "MOTOR OUTPUT VOLTAGE (−)" indicates the voltage of the power source line M−.

As illustrated in FIG. 3, the sequence of regeneration processing in the embodiment is divided into three sequences: (1) a sequence in a foot-switch not-stepped-on state; (2) a sequence in a foot-switch stepped-on state; and (3) a sequence in a regeneration control state. The foot-switch not-stepped-on state is a state where the motor 112 is stopped and the foot switch 201 is not stepped on. The foot-switch stepped-on state is a state where the foot switch 201 is stepped on. The regeneration control state is a state immediately after the state where the foot switch 201 is stepped on is switched to the state where the foot switch 201 is not stepped on.

In the foot-switch not-stepped-on state, the operating state signal is off. At this time, the drive controller 2021 does not control the motor 112. That is, the drive controller 2021 turns off the servo control signal to be input into the drive circuit 203. At this time, the motor relay 1122 also operates to bring the power source line M− to the disconnected state. Therefore, the motor 112 is in the free state. When the motor 112 is in the free state, the drive controller 2021 need not input the PWM data into the drive circuit 203. In the foot-switch not-stepped-on state, since the motor 112 does not rotate, the encoder signal (phase A and phase B) indicates a value shown at the time when the rotation of the motor 112 is stopped.

The monitoring unit 2022 of the control circuit 202 acquires the servo control signal and the encoder signal from the drive controller 2021 and inputs the servo control signal and the encoder signal into the regeneration controller 2023. The regeneration controller 2023 recognizes that the motor 112 is currently not controlled, based on the servo control signal being off, and recognizes that the motor 112 is currently stopped, based on the rotating speed indicated by the encoder signal. At this time, the regeneration controller 2023 turns off the regeneration control signal. The first regeneration resistor switching circuit 2042a is thereby turned off, and the first regeneration resistor 2041a is opened. Similarly, the second regeneration resistor switching circuit 2042b is also turned off, and the second regeneration resistor 2041b is opened.

In the foot-switch stepped-on state, the operating state signal is on. At this time, the drive controller 2021 controls the motor 112. That is, the drive controller 2021 receives the encoder signal output from the encoder 114. The drive controller 2021 then generates PWM data for controlling the magnitude of the voltage output from the drive circuit 203 so that the actual rotating speed of the motor 112 detected from the encoder signal matches the rotating speed corresponding to the amount of depression of the foot switch 201. The rotating speed corresponding to the amount of depression of the foot switch 201 is a rotating speed corresponding to the operating state signal. The drive controller 2021 then turns on a servo control signal for starting the drive of the motor 112 by the drive circuit 203 and inputs the servo control signal into the drive circuit 203 together with the PWM data.

The drive circuit 203 generates the voltage to be supplied to the motor 112 according to the PWM data from the drive controller 2021 and applies the generated voltage to the motor 112. This causes the motor 112 to rotate. By the rotation of the motor 112, the encoder signal (phase A and phase B) indicates a value corresponding to the rotating speed of the motor 112.

The regeneration controller 2023 recognizes that the motor 112 is currently controlled, based on the servo control signal being on. At this time, the regeneration controller 2023 keeps the regeneration control signal off.

In the foot-switch stepped-on state, the operating state signal is turned off when the depression of the foot switch 201 is released. That is, the drive controller 2021 turns off the servo control signal to be input into the drive circuit 203. At this time, the motor relay 1122 also operates to bring the power source line M− to the disconnected state. Therefore, the motor 112 is brought into the free state.

Here, while the motor 112 is rotating, the insertion section 101 self-propels against the body load. If the motor 112 becomes free in this state, there is a possibility that the influence of the body load causes the motor 112 to rotate in a reverse direction to the previous rotating direction. By such a reverse rotation (regeneration) of the motor 112, the motor 112 itself serves as an electric power generator to generate a regeneration voltage. FIG. 3 illustrates an example in which the regeneration causes the motor 112 to rotate backward, and a regeneration voltage occurs in the power source line M−. There is a possibility that such a regeneration voltage has an adverse effect on the drive circuit 203 and the like.

Hence, in the present embodiment, the protecting operation for protecting the sections of control apparatus 200 from the regeneration voltage is performed in the regeneration control state being a state immediately after the state where the foot switch 201 is stepped on is switched to the state where the foot switch 201 is not stepped on. Specifically, the regeneration controller 2023 recognizes that the control of the motor 112 is currently stopped since the servo control signal is switched from on to off. At this time, the regeneration controller 2023 turns on the regeneration control signal. The first regeneration resistor switching circuit 2042a is thereby turned on, and the first regeneration resistor 2041a is earthed. Similarly, the second regeneration resistor switching circuit 2042b is also turned on, and the second regeneration resistor 2041b is earthed. This causes, as illustrated in FIG. 2, a regeneration current RC corresponding to the regeneration voltage to flow to the ground via the regeneration resistor 2041. The regeneration voltage is thereby prevented from being applied to the drive circuit 203 and the like. Note that FIG. 2 illustrates an example in which the motor 112 rotates forward due to the regeneration. In this case, the regeneration current RC flows to the ground via the second regeneration resistor 2041*b*. In contrast, when the motor 112 rotates backward by the regeneration, the regeneration current RC flows to the ground via the first regeneration resistor 2041*a*.

Here, since the motor power source lines 1121 are near the encoder power source line 1141 as described above, there is a possibility that a short circuit fault occurs between a motor power source line 1121 and the encoder power source line 1141, as illustrated by S in FIG. 2. If a motor power source line 1121 is short-circuited to the encoder power source line 1141, current flows from the encoder power source line 1141 to the motor 112. If the regeneration resistor 2041 is earthed at this time, the encoder power source line 1141, the motor 112, the regeneration resistor 2041, and the ground form a closed circuit, and the motor 112 is thereby caused to rotate although the foot switch 201 is not stepped on.

The regeneration of the motor 112 occurs under the influence of the body load. Therefore, if the body load to the motor 112 disappears, the rotation of the motor 112 ends. After the rotation of the motor 112 has ended, there is no possibility that such the regeneration voltage has the adverse effect on the drive circuit 203 and the like even when the regeneration resistor 2041 is opened.

Hence, in the embodiment, the regeneration controller 2023 determines whether the motor 112 has been stopped, based on the encoder signal after short-circuiting the regeneration resistor 2041 (turning on the regeneration resistor switching circuit 2042). When determining that the motor 112 has been stopped, the regeneration controller 2023 then determines whether the predetermined set time has elapsed, and when determining the set time has elapsed, the regeneration controller 2023 turns off the regeneration resistor switching circuit 2042 to open the regeneration resistor 2041. This enables restraint on an unintended rotation of the motor 112 even when a short circuit thereafter occurs between a motor power source line 1121 and the encoder power source line 1141. Note that the set time may be a fixed time or may be set as appropriate according to, for example, a possible magnitude of the load. The magnitude of the load can be detected based on, for example, the magnitude of current supplied to the motor 112.

According to the embodiment, as described above, providing the regeneration protection circuit between the motor and the drive circuit enables the sections of the control apparatus such as the drive circuit to be protected from the regeneration voltage generated by the regeneration of the motor due to, for example, the influence of the body load.

In addition, in the embodiment, the protecting operation by the regeneration protection circuit is not performed at timings when the regeneration does not occur, such as in the foot-switch not-stepped-on state and in the foot-switch stepped-on state. By not performing the protecting operation by the regeneration protection circuit all the time, the load on the motor can be kept low as compared with a case where the regeneration resistor is always interposed.

In addition, in the present embodiment, the protecting operation by the regeneration protection circuit is configured not to be performed at a timing when the regeneration of the motor is considered to disappear in the regeneration control state. This enables restraint on an unintended rotation of the motor even when a short circuit occurs between a motor power source line and the encoder power source line. That is, in the foot-switch not-stepped-on state, the motor is in the free state, and thus the protecting operation by the regeneration protection circuit is not performed even when the short circuit occurs between a motor power source line and the encoder power source line. That is, since the regeneration resistor is not earthed, the motor does not rotate. In contrast, in the foot-switch stepped-on state, when the short circuit occurs between a motor power source line and the encoder power source line, the motor rotates also on the current from the encoder power source line. In this case, however, since the motor is under the control by the drive controller, the rotating speed of the motor is a rotating speed corresponding to the amount of depression of the foot switch even when the short circuit occurs between a motor power source line and the encoder power source line.

In addition, the regeneration protection circuit in the embodiment has a simple configuration comprising resistors and switches. This contributes to a reduction in size of the control apparatus. Furthermore, by making the regeneration protection circuit on the M+ side and the regeneration protection circuit on the M− side have the same configuration, the configuration of the control apparatus can be further simplified.

The invention has been explained based on the embodiment; however, the present invention is not limited to the embodiment. The present invention may be, of course, modified in various ways without departing from the gist and scope of the invention. For example, in the above-described embodiment, a rotating body for moving the insertion section 101 of the endoscope 100 forward and backward is the spiral tube 105. In contrast to this, the technique according to the present embodiment is applicable to various insertion devices that move the insertion section 101 forward and backward using a rotating body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A self-propelled endoscope apparatus, comprising:
    a rotation body provided on an outer peripheral surface of an elongated insertion section and configured to be rotatable;
    a motor configured to rotate the rotation body;
    a drive circuit configured to drive the motor; and
    a regeneration protection circuit configured to perform protecting operation for protecting the drive circuit from regeneration voltage generated by regeneration of the motor.

2. The self-propelled endoscope apparatus according to claim 1, wherein the rotation body is provided on the outer peripheral surface of the insertion section and configured to be rotatable around a longitudinal axis.

3. The self-propelled endoscope apparatus according to claim 1, further comprising
    a control circuit configured to:
        monitor an operating state of the motor; and
        control the protecting operation by the regeneration protection circuit based on a result of the monitoring.

4. The self-propelled endoscope apparatus according to claim 3, wherein the control circuit performs control such that the protecting operation by the regeneration protection circuit is started when it is detected that drive of the motor by the drive circuit is stopped, and performs control such that the protecting operation by the regeneration protection circuit is ended after a lapse of a predetermined set time since stop of the motor is detected.

5. The self-propelled endoscope apparatus according to claim 1, wherein the drive circuit brings the motor into a free state while the protecting operation by the regeneration protection circuit is performed.

6. The self-propelled endoscope apparatus according to claim 3, wherein
the regeneration protection circuit comprises:
a regeneration resistor comprising a first terminal connected in parallel to a power source line between the motor and the drive circuit, and a second terminal connected to a ground; and
a regeneration resistor switching circuit provided between the regeneration resistor and the ground and configured to short circuit or open between the regeneration resistor and the ground according to a control signal from the control circuit.

7. The self-propelled endoscope apparatus according to claim 6, wherein
the power source line comprises a first power source line for supplying electric power to cause the motor to rotate forward and a second power source line for supplying electric power to cause the motor to rotate backward,
the regeneration resistor comprises a first regeneration resistor comprising a third terminal that is connected in parallel to the first power source line and a fourth terminal that is connected to the ground, and a second regeneration resistor comprising a fifth terminal that is connected in parallel to the second power source line and a sixth terminal that is connected to the ground,
the regeneration resistor switching circuit comprises a first regeneration resistor switching circuit configured to short circuit or open between the first regeneration resistor and the ground, and a second regeneration resistor switching circuit configured to short circuit or open between the second regeneration resistor and the ground, and
the first regeneration resistor and the second regeneration resistor have a same resistance value.

8. A control apparatus for a self-propelled endoscope apparatus that comprises a rotation body provided on an outer peripheral surface of an insertion section and configured to be rotatable, and a motor configured to rotate the rotation body, the control apparatus comprising:
a drive circuit configured to drive the motor; and
a regeneration protection circuit configured to perform protecting operation for protecting the drive circuit from regeneration voltage generated by regeneration of the motor.

9. The control apparatus for a self-propelled endoscope apparatus according to claim 8, further comprising
a control circuit configured to:
monitor an operating state of the motor; and
control the protecting operation by the regeneration protection circuit based on a result of the monitoring.

10. The control apparatus for a self-propelled endoscope apparatus according to claim 9, wherein the control circuit performs control such that the protecting operation by the regeneration protection circuit is started when it is detected that drive of the motor by the drive circuit is stopped, and performs control such that the protecting operation by the regeneration protection circuit is ended after a lapse of a predetermined set time since stop of the motor is detected.

11. The control apparatus for a self-propelled endoscope apparatus according to claim 8, wherein the drive circuit brings the motor into a free state while the protecting operation by the regeneration protection circuit is performed.

12. The control apparatus for a self-propelled endoscope apparatus according to claim 9, wherein
the regeneration protection circuit comprises:
a regeneration resistor comprising a first terminal connected in parallel to a power source line between the motor and the drive circuit, and a second terminal connected to a ground; and
a regeneration resistor switching circuit provided between the regeneration resistor and the ground and configured to short circuit or open between the regeneration resistor and the ground according to a control signal from the control circuit.

13. The control apparatus for a self-propelled endoscope apparatus according to claim 12, wherein
the power source line comprises a first power source line for supplying electric power to cause the motor to rotate forward and a second power source line for supplying electric power to cause the motor to rotate backward,
the regeneration resistor comprises a first regeneration resistor comprising a third terminal that is connected in parallel to the first power source line and a fourth terminal that is connected to the ground, and a second regeneration resistor comprising a fifth terminal that is connected in parallel to the second power source line and a sixth terminal that is connected to the ground,
the regeneration resistor switching circuit comprises a first regeneration resistor switching circuit configured to short circuit or open between the first regeneration resistor and the ground, and a second regeneration resistor switching circuit configured to short circuit or open between the second regeneration resistor and the ground, and
the first regeneration resistor and the second regeneration resistor have a same resistance value.

14. A method for controlling a rotation body, comprising:
detecting a driving state of a motor configured to rotate the rotation body;
performing protecting operation for protecting a drive circuit for the motor from regeneration voltage generated by regeneration of the motor when it is detected that the motor is stopped; and
ending the protecting operation after a lapse of a predetermined time since stop of the motor is detected.

* * * * *